US008182806B2

(12) United States Patent　　(10) Patent No.: US 8,182,806 B2
Johnson　　(45) Date of Patent: *May 22, 2012

(54) SYNOVIAL VILLI FOR USE WITH TISSUE ENGINEERING

(76) Inventor: Lanny L. Johnson, Okemos, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/848,987

(22) Filed: Aug. 2, 2010

(65) Prior Publication Data

US 2011/0002904 A1　　Jan. 6, 2011

Related U.S. Application Data

(63) Continuation-in-part of application No. 11/210,077, filed on Aug. 23, 2005, now Pat. No. 7,785,582.

(60) Provisional application No. 60/622,446, filed on Oct. 27, 2004, provisional application No. 60/607,676, filed on Sep. 7, 2004.

(51) Int. Cl.
　　*A01N 63/00*　　(2006.01)
(52) U.S. Cl. ............... 424/93.7; 424/9.363; 424/537; 424/156.1
(58) Field of Classification Search ............... 424/93.7
See application file for complete search history.

(56) References Cited

U.S. PATENT DOCUMENTS

| | | |
|---|---|---|
| 4,141,973 A | 2/1979 | Balazs |
| 4,213,816 A | 7/1980 | Morris |
| 4,489,055 A | 12/1984 | Couvreur et al. |
| 5,004,681 A | 4/1991 | Boyse et al. |
| 5,079,236 A | 1/1992 | Drizen et al. |
| 5,192,553 A | 3/1993 | Boyse et al. |
| 5,197,985 A | 3/1993 | Caplan et al. |
| 5,226,914 A | 7/1993 | Caplan et al. |
| 5,577,513 A | 11/1996 | Van Vlasselaer |
| 5,811,094 A | 9/1998 | Caplan et al. |
| 5,842,477 A | 12/1998 | Naughton et al. |
| 5,908,784 A | 6/1999 | Johnstone et al. |
| 6,080,194 A | 6/2000 | Pachence et al. |
| 6,174,333 B1 | 1/2001 | Kadiyala et al. |
| 6,203,576 B1 | 3/2001 | Afriat et al. |
| 6,322,588 B1 | 11/2001 | Ogle et al. |
| 6,387,369 B1 | 5/2002 | Pittenger et al. |
| 6,461,645 B1 | 10/2002 | Boyse et al. |
| 6,569,427 B1 | 5/2003 | Boyse et al. |
| 6,602,294 B1 | 8/2003 | Sittinger et al. |
| 6,605,275 B1 | 8/2003 | Boyse et al. |
| 6,699,471 B2 | 3/2004 | Radice et al. |
| 2002/0122790 A1 | 9/2002 | Hunziker |
| 2003/0130250 A1 | 7/2003 | Bridger et al. |
| 2004/0028717 A1 | 2/2004 | Sittinger et al. |
| 2004/0142465 A1 | 7/2004 | Radice et al. |
| 2007/0059372 A1 | 3/2007 | Johnson |
| 2007/0253938 A1* | 11/2007 | Ciombor et al. ............ 424/93.7 |
| 2010/0196331 A1 | 8/2010 | Johnson |

OTHER PUBLICATIONS

De Bari et al. Failure of In Vitro—Differentiated Mesenchymal Stem Cells From the Synovial Membrane to Form Ectopic Stable Cartilage In Vivo, Arthritis & Rheumatism, vol. 50, No. 1, Jan. 2004, pp. 142-150.*

Lolito et al., Consumption of flavonoid-rich foods and increased plasma antioxidant capacity in humans: Cause, consequence, or epiphenemenon, Free Radical Biology & Medicine 2006, 41:1727-1746.

Miller et al., Chondroprotective effects of a proanthocyanidin rich Amazonian genonutrient reflects direct inhibition of matrix metalloproteinases and upregulation of IGF-1 production by human chondrocytes, Journal of Inflammation 2007, 4:16.

Miller et al., The chondroprotective actions of a natural product are associated with the activation of IGF-1 production by human chondrocytes despite the presence of IL-1B, BMC Complementary and Alternative Medicine 2006, 6:13.

Jayaprakasam et al., Insulin secretion by bioactive anthocyanins and anthocyanidins present in fruits, J. Agric. Food Chem, 2005, 53:28-31.

Frei, Studies force new view on biology of flavinoids, Eureka Alert Mar. 5, 2007.

Reeves et al., Randomized, prospective, placebo-controlled double-blind study of dextrose prolotherapy for osteoarthritic thumb and finger (DIPP, PIP, and Trapeziometacarpal) joints: evidence of clinical efficacy, Journal of Alternative and Complementary Medicine, 2000, 6(4):311-320.

Utterlinden et al., Glucosamine increases hyaluronic acid production in human osteoarthritic synovium explants, BMC Mucoskeletal Disorders 2008, 9:120.

Rovensky et al., Clin. Exp. Rheumatol. May-Jun. 2005, Abstract.
Nagata et al., Biochem. Biophys. Res. Commun. 318:625-30.
Chen, Arthritis Res Ther., 2008;10(5):223 (abstract only).
Crawford, European Cells and Materials, vol. 16 Suppl. 2, 2008, p. 41 (abstract only).
De Bari, Arthritis Rheum. 2001; 44(8):1928-42 (abstract only).
Jones, Arthritis Rheum. 2004; 50(3):817-27 (abstract only).
Jones, Arthritis Rheum. Jun. 2008; 58(6):1731-40 (abstract only).
McGonagle, Rheumatology 2008; 47(8):1114-1116.
Keyzer et al., Rheumatol. Feb. 1995; 22(2):271-81.
Schneiderman et al., Arch. Biochem. Biophys. Dec. 1995; 324 (1):173-88.
Schmidt et al., Osteoarthritis Cartilage May 2006; 14(5):403-12.
Taylor et al., Febs Lett. 1988; 236:33-8.
Fortier et al., J. Bone and Joint Surg. Mar. 2002; 84B(2):276-88.
Matsumoto et al., Journal of Clinical Endocrinology and Metabolism 1996; 81:150-5.
Dore et al., Arthritis and Rheumatism 1995; 38(3):413-419.
Smith et al., British Medical Journal 2000; 321:847-48.
Kellner et al., J. Drug Target 2001; 9(6):439-8.
Cai et al., Osteoarthritis Cartilage Sep. 2002; 10(9):692-706.
Suzuki et al., PNAS 10.1073/pnas.0936260100 (Aug. 2003).
Fasutman et al., Science Nov. 2003; 302:1123-27.

(Continued)

*Primary Examiner* — Jon P Weber
*Assistant Examiner* — Tiffany Gough
(74) *Attorney, Agent, or Firm* — Michael J. Gallagher; David J. Dawsey; Gallagher & Dawsey Co., LPA (57) ABSTRACT

Synovial villi derived explants and related surgical tools used to repair or prevent damage to injured or diseased tissue, including connective tissue. The tools including a harvesting tool for selectively harvesting synovial villi from the joint of patient and a delivery tool having a bulbous end for delivering the synovial villi derived explants while reducing damage to surrounding tissue.

27 Claims, 4 Drawing Sheets

OTHER PUBLICATIONS

Rovensky et al., Clin. Exp. Rheumatol. May-Jun. 2005, Abstract.
Sakaguchi et al., Arthritis & Rheumatology. Aug. 2005, Abstract.
Scheffold et al., Blood, 1999; 94 (suppl. 1): 664a.
Vandenbeele et al., Arch. Histol. Cytol., May 2003; 66(2): 145-150.
Hunziker et al., J. Bone Joint Surg. Am., May 1996, 78(5):721-33.
Johnson, Arthroscopic Surgery Principles and Practice, C.V. Mosby, 1986, St. Louis (pp. 173-245).
Morito, Rheumatology 2008; 47(8):1137-1143 (abstract only).
Pei, Clin Orthop Relat Res. 2008; 466(8):1880-9.
Mehbood et al., Journal of Clin. Investig. Mar. 2003; 111(6).
Nagata et al., Biochem. Biophys. Res. Commun. 318:625-30, 2004.
Collins et al., Clinical and Diagnostic Laboratory Immunology, vol. 3, 1996, pp. 5-9.
De Bari et al., Arthritis & Rheumatism, Aug. 2001; 44(8): pp. 1928-42.
De Bari et al., Journal of Cell Biology 160:6 909-918 (2003).
Key, J. Bone Joint Surg., 7:793 (1925).
Kowalczyk et al., Presentation at Symposium E, 2003; 07-21; 13:17.
Luyten et al., Best Practice and Research Clinical Rheumatology, vol. 15, 2001, pp. 759-769.
Nishimura et al., Arthritis & Rheumatism, vol. 42, 1999, pp. 2631-2637.
Perry et al., Cardiovascular Tissue Engineering, J. Cardiovasc. Nurs. 2003; 18:330-37.
Quesenberry et al., Proc. Natl.Acad. Sci. USA, vol. 95, pp. 15155-15157 (1998).

* cited by examiner

SYNOVIAL VILLI FOR USE WITH TISSUE ENGINEERING

CROSS REFERENCE TO RELATED APPLICATIONS

This application is a continuation-in-part of U.S. patent application Ser. No. 11/210,077 filed on Aug. 23, 2005, which claims benefit of priority to U.S. provisional patent application Ser. Nos. 60/622,446 filed on Oct. 27, 2004 and 60/607,676 filed on Sep. 7, 2004; the contents of which are herein incorporated by reference in their entirety

TECHNICAL FIELD

The invention relates to methods and tools for the treatment of damaged or diseased tissue by harvesting synovial villi from a patient to form an explant and delivering the explant to the damaged tissue, optionally together with an implantable device.

BACKGROUND OF THE INVENTION

There are various types of cartilage, e.g., hyaline cartilage and fibrocartilage. Hyaline cartilage is found at the articular surfaces of bones, e.g., in the joints, and is responsible for providing the smooth gliding motion characteristic of moveable joints. Articular cartilage is firmly attached to the underlying bones and typically measures less than 5 mm in thickness in human joints, with considerable variation depending on joint and site within the joint. Additionally, articular cartilage is aneural, avascular, and alymphatic. In adult humans, cartilage derives its nutrition by a double diffusion system through the synovial membrane and through the dense matrix of the cartilage to reach the chondrocyte, the cells that are found in the connective tissue of cartilage.

Adult cartilage has a limited ability of repair; thus, damage to cartilage produced by disease, such as rheumatoid and/or osteoarthritis (OA), or trauma can lead to serious physical deformity and debilitation. Furthermore, as human articular cartilage ages, its tensile properties change. For instance, the superficial zone of the knee articular cartilage exhibits an increase in tensile strength up to the third decade of life, after which it decreases markedly with age as detectable damage to type II collagen occurs at the articular surface. The deep zone cartilage also exhibits a progressive decrease in tensile strength with increasing age, although collagen content does not appear to decrease. These observations indicate that there are changes in mechanical and, hence, structural organization of cartilage with aging that, if sufficiently developed, can predispose cartilage to traumatic damage.

Depending on the severity of the damage, affected joints may require surgical intervention. In some instances portions of the joint are sutured together to facilitate healing. In other instances, total joint replacement is necessary. In still other instances, implants short of total replacement are inserted. For example, U.S. Pat. No. 6,080,194 to Pachence et al. discloses a porous collagen-based implant for use in the repair of cartilage lesions. Specifically, Pachence proposes using a porous collagen sponge with a dense collagen membrane. The dense collagen membrane is provided as a barrier against movement of cells from the subchondral plate while the sponge permits the ingrowth of cells. U.S. Pat. No. 6,602,294 B1 to Sittinger et al. proposes implantable substrates for the healing and protection of connective tissue, preferably cartilage. The substrate includes a growth and differentiating factor, a chemotactic factor, a cellular adhesion molecule and a structure such as hydrogel or a sponge. U.S. Pat. No. 5,842,477 to Naughton et al. proposes methods for repairing cartilage by implanting a biocompatible scaffold in combination with periosteal and/or perichondrial tissue to provide a source of chondrocyte progenitor cells, chondrocytes and other stromal cells for attachment to the scaffold.

While many approaches to treat injured joints involve the surgical insertion of an implant, others have proposed the direct transfer of endogenous tissue housing synovial cells, without the need of an additional substrate. For instance, U.S. 2002/0122790 to Hunziker proposes the treatment of cartilage defects including surgically removing sheets of synovial tissue from the patient and introducing the entire sheet at the site of defect. While this approach effectively transfers synovial cells, additional beneficial cells or factors absent in the normal synovium must be added to advance the technique, which includes further surgical processes or culturing techniques.

Accordingly there remains a need to identify alternative approaches to the treatment of damaged or diseased tissue, which delivers a cocktail of beneficial cells, tissues or factors that together enhance recovery from surgical procedures. Further, there remains a need to effectively harvest these beneficial components and deliver them to sites requiring the generation of new tissue.

BRIEF SUMMARY OF THE INVENTION

The present invention provides explants, therapeutic compositions, tools and their use to repair or prevent further damage to injured or diseased tissue, including connective tissue. As such, a tissue engineering system is developed that promotes the healing of cartilage, ligaments and the like, which may be used to treat various associated medical conditions, such as forms of arthritis that would otherwise potentially lead to joint replacement.

The above goals are accomplished by providing methods, compositions and tools for treating a patient to repair damaged or diseased tissue, which includes harvesting synovial villi, or portions thereof, from a synovial membrane of a joint of the patient to provide an explant; and introducing the explant to the damaged or diseased tissue so as to repair the tissue. Preferably, the introduced explant includes synovial villi and all of its harvested components. A variety of connective tissues and conditions of the joint may be treated including those associated with articular cartilage, a meniscus, a ligament and the like. Further, in preferred embodiments each harvested portion of synovial villi includes at least 50% of the entire protrusion extending into the joint cavity from the base synovial lining. Accordingly, beneficial factors found within the synovial villi can be effectively harvested and transferred as part of the explant. In some instances synovial villi are harvested from the same joint as the tissue to be treated.

Harvest is preferably selective to prevent or reduce damage of the base synovial membrane disposed between the synovial villi in the joint. Thus, in addition to targeting the beneficial villi, selective harvest reduces the severity of injury at the harvest site. As such, selectively harvesting synovial villi from the joint prevents compromising the joint capsule integrity, which further reduces the likelihood of a synvovial hernia or leak of synovial fluid post op. In an exemplary embodiment selective harvest is performed using a harvesting tool, which includes a hollow shaft having at one end a plurality of apertures for receiving synovial villi and a cutting means for surgical removal of received villi. Harvest may also include an aspiration means or step where excised or cut portions of synovial villi are collected from an aspirate. In some embodiments the portions of synovial villi are collected in a trap resembling a syringe body. In another embodiment harvesting synovial villi is performed using a harvesting tool including a syringe body engaged to a needle having a bulbous tip. Synovial fluid may also be collected for later culturing or co-administration.

Preferred explants include synovial villi and all of its harvested components. The harvested components include cell or tissue types captured from the villi which can assist in the formation of new tissue. The harvested components preferably include blood vessels, which may include whole blood, red blood cells, white blood cells, angioblasts, electrolytes, clotting factors, fibrinogen, growth hormones and growth factors such as, but not limited to, Insulin-like growth factor 1 (IGF-1). The harvested components also preferably include adipose tissue or cells therefrom, which may include stem cells or progenitor cells. If aspirating the joint to harvest synovial villi, the synovial fluid may also be collected and thus stem cells, which have an increased presence in instances of joint damage, may also be harvested. Thus, stem cells obtained from the synovial villi and the synovial fluid may be collected and provided as the explant.

The explant may be introduced directly to the damaged or diseased tissue without further culturing or expansion of cells collected from the harvested synovial villi. Introduction may occur under direct vision, intra articularly by arthrocentesis, during arthroscopic surgery and the like. Further, synovial villi may be minced or morcellized prior to delivery, which may occur concurrently during harvest, such as via the cutting means. Alternatively, the harvested synovial villi may be cultured, treated or morcellized ex vivo prior to delivery. In some embodiments, the synovial villi are cultured in the presence of one or more growth factors, such as IGF-1 prior to introduction to the patient. In other embodiments, synovial villi are cultured or treated with one or more of an anthocyanin, an anthocyanidin and dextrose. An anthocyanin or anthocyanidin and optionally dextrose may be administered to the joint together with the explant as a combined treatment, which may result in increased levels of IGF-1. In other embodiments, synovial fluid is collected, beneficial cells are isolated, then introduced to synovial villi under culture conditions or for co-delivery.

In a related embodiment a method of treating a patient to repair damaged or diseased tissue includes harvesting a plurality of synovial villi from a synovial lining of a joint of the patient without substantially removing the synovial lining between the plurality of synovial villi; and introducing an explant of collected synovial villi to the damaged or diseased tissue so as to repair the tissue.

In some instances the amount of beneficial components, such as beneficial cells or growth factors, found in the synovial villi can be increased by pretreating the patient with one or more compositions that stimulate or increase their production or localization at the synovial villi. Compositions such as IGF-1 and anthocyanins or anthocyanidins and optionally dextrose may increase local concentration of beneficial components.

Further, the tissue engineering system may include methods and tools that harvest synovial villi from a joint of the patient to provide an explant; introduce the explant to an implantable surgical device; and implant the surgical device so as to repair the damaged or diseased tissue, wherein the implanted surgical device houses or provides synovial villi and preferably all of its harvested components. The implantable surgical device may be any suitable scaffolding or substrate to enhance delivery or growth of cells or tissue at the site of treatment. For instance, the implantable surgical device may be an implantable sponge, collagen matrix and the like. In some embodiments, the implantable surgical device includes a replacement ligament or replacement meniscus, which may itself include a biocompatible, biodegradable or bioabsorbable material. For instance, the meniscus may include collagen or a type 1 collagen. The meniscus may include a porous polymer or a bioplastic.

The tissue engineering system can be used to treat a variety of damaged tissues such as a sternoclavicular meniscus, an acromioclavicular meniscus, a tempromandibular meniscus, and a radioulnar meniscus. Alternatively, the system may treat a joint labrum, a shoulder labrum or a hip labrum. Treatment methods may be used alone or combined with other procedures such as a microfracture surgery, arthroscopic abrasion surgery or arthroplasty surgery to enhance treatment.

In a related aspect, an implantable surgical device cultured in the presence of synovial villi harvested from a joint of a patient without the presence of a base synovial membrane is provided. The base synovial membrane refers to a region of the synovium surrounding the synovial villi at a site of harvest.

In another related aspect, a surgical kit for use in performing a meniscus replacement procedure is provided, which includes: a harvesting tool for selectively harvesting synovial villi from a synovial lining of a joint, the harvesting tool including a hollow shaft including at one end a plurality of apertures for receiving synovial villi and a cutting means for surgical removal of received villi; a delivery needle including a proximal end for attachment to a syringe and a bulbous distal end having a delivery aperture; and optionally an implantable surgical device, such as a replacement meniscus. The kit may also include a syringe for use as a collecting or delivery body, which can engage the needle, optionally with a removable stopper having two apertures for communication with the harvesting tool and a vacuum source.

In another related aspect, an apparatus for collecting and delivering synovial villi, is provided, which includes: a syringe body including a removable stopper at a first end, the removable stopper optionally having two apertures, wherein a first aperture is able to connect to a vacuum source and a second aperture able to communicatively connect to a hollow collection shaft, the second end of the syringe including a connector, such as a luer connector; a syringe plunger reversibly insertable with the first end of the syringe when the stopper is removed; and a delivery needle including a complementary connector, such as a luer connector at a first end for reversible engagement with the connector of the syringe and a bulbous second opposing end including a delivery aperture.

In a related embodiment an apparatus for collecting synovial villi is provided, which includes a syringe and a syringe needle, wherein the syringe needle has a bulbous distal end with an aperture angled between 10 and 180 degrees from the plane of the needle, more preferably between 90 and 135 degrees.

In another related embodiment a device for harvesting synovial villi from a joint of a patient is provided, which includes a flexible or rigid shaft member having at its distal end a plurality of apertures for collecting synovial villi and a cutting means for cutting collected synovial wherein the device is coupled to an aspirating source or a vacuum source.

BRIEF DESCRIPTION OF THE DRAWINGS

FIGS. 8a-8d depict a collection/delivery apparatus shown in a delivery configuration 40. FIG. 8a depicts a bulbous end 44 with a delivery aperture at 90 degrees 48a.

DETAILED DESCRIPTION OF THE INVENTION

The present invention addresses the need to develop methods, compositions and tools to repair damaged or diseased tissue, such as connective tissue. Specifically, the methods, compositions and tools provide a comprehensive system for tissue engineering using synovial villi derived explants. The system permits the user to exploit the beneficial components found in the synovial villi and provides tools that effectively lead to their harvest and delivery to sites requiring the generation of new tissue. As nonlimiting examples, this tissue engineering system treats medical conditions associated with connective tissue, such as osteoarthristis, which can assist in repair after traumatic injury of the connective tissue, and to enhance healing after a surgical procedure, such as microfracture surgery, arthroscopic abrasion surgery, arthroplasty surgery, and the like.

A. Definitions

All patents, patent applications, government publications, government regulations, and literature references cited in this specification are hereby incorporated herein by reference in their entirety. In case of conflict, the present description, including definitions, will control.

The term "pluripotent" used herein refers to cells which have developmental plasticity and are capable of giving rise to cells derived from any of the three embryonic germ layers, including the mesoderm, endoderm, and ectoderm.

The term "stem cells" used herein refers to undifferentiated cells which are capable of dividing and self-renewal for extended periods, are unspecialized, and can differentiate into many lineages of specialized cell types.

The term "progenitor cells" used herein refers to unspecialized or partially specialized cells differentiated from stem cells or other cell types and which have the capacity to divide into more than one specialized cell type.

The term "omentum" used herein refers to the fold in the peritoneum which supports the viscera and blood vessels within the abdominal cavity.

The terms "selectively harvesting" and "without substantially removing the synovial lining between the plurality of synovial villi" as used herein refer to the controlled excision or removal of synovial villi while the surrounding synovium remains intact. Selective harvest is performed by capturing the inward extending protrusions characteristic of synovial villi.

The term "biodegradation" or "biodegradable" refers to hydrolytic, enzymatic, and other metabolic degradation processes in the living organism, which are primarily caused by the bodily fluids which come into contact with the biodegradable material of the implant, resulting in gradual disintegration of the structures of the implant containing the biodegradable material. As a result of this process, at a certain point in time the implant loses its mechanical integrity. The term "bioabsorption" or "bioabsorbable" includes the subsequent absorption of the degradation products by the living organism.

B. Use of Synovial Villi for the Treatment of Damaged or Diseased Tissue

Synovium constitutes the lining of synovial joints. It includes synovial cells covering a lining of fat and vascularity. These synovial cells can have pleuripotential healing capacity from primitive fibroblasts to fibrous tissue to cartilage cells. Human mutlipotent mesenchymal stem cells (MSCs) have been isolated from the synovial membrane of knee joints. DeBari et al., Arthritis Rheum., 2001; 44(8): 1928-42. In some instances of joint inflammation the lining proliferates into fingerlike projections called villi. Although synovial villi are primarily found in instances of inflammation from degenerative arthritis and traumatic injuries, synovial villi are transient and thus do not always populate a joint suffering from injury or disease. Accordingly, in some instances inflammation will be present in the joint, yet the synovial villi are absent.

All the ingredients of the normal synovium are present in the synovial villi. In addition within the villi is increased vascularity due to angioblastic proliferation, increased cellularity, and increased fluids due to response to injury or disease. Further, there can be increased repair cells, including stem cells at and/or near the injury site. Typically, there are also growth hormones accompanying natural repair process. If there was trauma, there may be increased clotting factors and fibrinogen, as well as the resultant fibrin mesh for cellular repair or reconstruction. Depending upon the interval between injury and repair, there can also be fibroblasts or fibrous tissue. Further, while the synovial villi have increased vascularity and cellularity, the villi also release the beneficial components into the surrounding synovial fluid.

Accordingly, while synovial cells from normal synovium may be used to form chondrocytes and thus assist in the repair of cartilage, in addition to synovial cells the finger-like reactive projections of the synovium provide a rich source of beneficial cells and factors, which may be harvested and exploited for enhanced or improved treatment of connective tissue. For instance, harvested synovial villi may include stem cells, fibroblasts, monocytes, lymphocytes, angioblasts, circulating growth factors, such as Insulin-like growth factor 1 (IGF-1), electrolytes, clotting factors, fibrinogen, growth hormones, and the like which may be used to stimulate growth or repair of cartilage, ligaments, and the like. Thus, while synovial cells provide a beneficial therapy themselves, the combination of synovial cells together with additional components which are obtained when harvesting synovial villi further enhances the healing capabilities of explants. As such, harvesting and delivery of the synovial villi itself enhances repair and protection of damaged or diseased tissue.

A variety of damaged or diseased tissue may be treated, especially those affecting connective tissue. As such, the methods and compositions treat or ameliorate symptoms associated with a variety of conditions affecting a patient's joint. Among these include methods and compositions for the prevention or treatment of cartilage-associated conditions or disorders of the hand, foot, ankle, knee, hip, spine, growth plates, intervertebral disc and the like. Further, the treatments are particularly useful for cartilage disorders or cartilage-associated medical conditions such as arthritis, and more particularly traumatic and osteoarthritis. Additional examples include treatments for adverse conditions affecting cartilage, which includes articular cartilage, a ligament, a meniscus, which includes a sternoclavicular meniscus, an acromioclavicular meniscus, a tempromandibular meniscus, and a radioulnar meniscus, and the like. Conditions such as lupus and rheumatoid arthritis may also benefit from such treatment as will genetic or post surgical conditions that result in damaged cartilage.

Preferably, the methods and compositions are used for the treatment of humans. However, the methods and compositions are also useful in the veterinary arts, such as for the treatment of animals and in particular mammals. A variety of cartilage-associated disorders are prevalent in mammals, including in *equine* or horse and *canis* or dog. As such, the methods and compositions will also be useful for the treatment of a variety of mammals, including horses, dogs, cats, livestock, humans and the like.

In a preferred method, synovial villi or portions thereof are harvested from a synovial membrane of a joint of the patient to provide an explant; and subsequently introduced to the damaged or diseased tissue so as to repair the tissue. Preferably, the introduced explant includes synovial villi and all of its harvested components. That is, while the treatment methods may vary, preferably each includes harvesting of synovial villi, which includes synovial cells as well as additional beneficial components, which themselves are found within the blood vessels or fatty regions of the villi. The amounts and identity of each beneficial component may vary; however, they may include fibroblasts, lymphocytes and angioblasts, red blood cells, white blood cells, electrolytes, clotting factors, fibrinogen, growth hormones and growth factors such as, but not limited to, Insulin-like growth factor 1 (IGF-1), stem cells and progenitor cells.

While not preferred, a portion of the synovium membrane containing villi could be surgically removed, followed by harvest of the villi from the excised membrane. Preferably however, synovial villi are selectively harvested directly from the patient without removal of the surrounding synovial membrane. Since the villi are transient and thus not always present, even in instances of inflammation, the physician may wish to confirm the presence of synovial villi in regions of the synovium to consider appropriate sites for harvest. This is facilitated by their anatomical structure, which permits their identification. That is, close visual inspection of the synovial membrane under conventional magnification will reveal the presence or absence of synovial villi. While synovial villi may be identified, their transient nature and varying locations may require thorough inspection of the joint. That is, synovial villi may be found at some regions of the knee and not others. Most often synovial villi, if present, will be found in the medial or lateral recesses of the knee.

While harvesting synovial villi provides an improved approach for the treatment of tissue damaged by injury or disease, the ability of the body to naturally rebuild synovium from sites of harvest adds to the desirability of its use. For example, the synovium itself can regenerate after complete removal. (Key, J. Albert, The reformation of synovial membrane in the knees of rabbits after synovectomy. J. Bone Joint Surg. 7:793. 1925). Further, it has also been reported by Hunziker and Rosenberg that synovium will grow over cartilage and heal a laceration in cartilage (J. Bone Joint Surg. Am. 1996 May; 78(5):721-33). Accordingly, in addition to the improved treatment through the use of synovial villi itself, the selective harvest of synovial villi from the synovial membrane will retain portions of the surrounding synovium at the site of harvest thereby enhancing regeneration of synovium at the site of removal. Thus, in a preferred approach, protrusions of the synovium are selectively harvested while regions of the synovium between harvested protrusions preferably remain at the site of harvest. This can be accomplished using a harvesting tool that selectively removes the finger-like projections of the synovium while regions between the harvested protrusions substantially remain at the site of harvest. While it is preferred to harvest as much of each targeted finger-like projection as possible, the physician should at least harvest the lining of synovial cells and at least some fat. Most preferably, blood vessels within each targeted projection are also harvested to provide additional beneficial components found in local circulation.

Harvesting synovial villi may be accomplished using a variety of approaches. For example, harvesting synovial villi can include aspiration of identified regions of the knee, most often the medial or lateral recesses of the knee. Aspiration provides a further benefit when performed in a liquid medium since collected material is naturally washed. While aspiration is used to harvest the villi, the skilled artisan will realize surrounding synovial fluid will also be collected. This surrounding synovial fluid will often contain beneficial cells such as stem cells, which may be delivered to the patient with or as part of the explant. That is, the presence of synovial villi correlates with an increase of free floating stem cells in the surrounding synovial fluid. For instance, patients suffering from osteoarthritis were demonstrated to have a higher prevalence of mesenchymal progenitor cells (MPCs) in the synovial fluid, which is believed to originate from disrupted joint structures. Jones et al., Arthritis Rheum 2004; 50(3):817-27. In a later study, it was also found that increased mesenchymal stem cells (MSCs) in early osteoarthritis correlated with numbers of free microscopic tissue fragments. Jones et al., Arthritis Rheum. 2008 June; 58(6):1731-40. In another study, synovial fluid harvested from 19 knee joints with anterior cruciate ligament injury around the time of reconstruction surgery and from three healthy volunteers was compared, and it was found that the ligament injury patients had 100 times more MSCs than normal volunteers. Morito et al., Rheumatology 2008 47(8):1137-43. The sources of free floating stem cells in synovial fluid is believed to originate from the synovium itself. Further, since synovial villi can be found in disrupted joint structures and are formed in response to non-reactive synovium engulfing small particles of cartilage that flake off from the joint, the presence of synovial villi is a useful indicator in determining the presence of stem cells in the synovial fluid.

Among the beneficial components found in the synovial villi, stem cells may be some of the more active in the repair process. Mesenchymal stem cells (MSCs) have been harvested from marrow, periosteum and muscle connective tissue. Recently, stem cells have been identified outside of the marrow in a variety of tissues including fatty tissue and in the circulating blood. This discovery lead to the advent of chemical substances such as filgrastim (G-CSF) and AMD3100 that can be injected into the patient and increase the yield of progenitor cells in the peripheral blood. Thus, pretreating the patient with compositions prior to harvesting synovial villi may increase stem cell populations in the villi or synovial fluid. AMD3100 bicyclam compound (AnorMED Inc., Langley, British Columbia, Canada) is a small molecule described in U.S. Patent Application Publication No. 2003/0130250 to Bridger et al. that inhibits stromal cell derived factor-1 (SDF-1) binding to its receptor CXCR4 on CD34+ cells currently in clinical trials. U.S. Provisional Patent Application Ser. No. 60/607,676 to Johnson, hereby incorporated herein by reference in its entirety, describes other methods of mobilizing stem and progenitor cells. Stem cells have also been isolated by density-gradient centrifugation from bone marrow aspirates. Mesenchymal stem cells have been shown to adhere to polystyrene while other cells found in bone marrow aspirates, i.e. cells of hematopoietic lineage do not adhere to polystyrene tissue culture materials.

As introduced above, prior to harvest the joint may be pretreated with compositions to increase the availability of one or more beneficial components. Thus, one approach is to increase a cellular component such as increasing the availability of stem cells or progenitor cells. Another approach is to increase levels of IGF-1 in the synovial villi or in the surrounding synovial fluid. IGF-1 is naturally present in the synovium. Keyzer et al., Rheumatol. 1995 February; 22(2) 271-81. It is also found in the synovial fluid. Schneiderman et al., Arch Biochem Biophys 1995 December; 324(1):173-88. Accordingly, activation of IGF-1 prior to harvest could increase its yield either in the villi or in the synovial fluid. Approaches to increasing activation of IGF-1 are discussed below, and are incorporated herein. Among these include administration of insulin or administration of an anthocyanin or anthocyanidin, optionally with dextrose (or glucose).

Once harvested, the synovial villi may be used en toto as the explant itself without further treatment. That is, once harvested the synovial villi and its harvested components may be used as an explant in an immediate implantation procedure. In such an example, the explant is positioned over or proximate to the site of the defect and may optionally be accompanied by transforming factors, growth factors, such as IGF-1, reparative or protective compositions and the like. Further, the synovial villi may be morcellized or minced then replanted. Once delivered, synovial cells obtained from villi can themselves differentiate into chondrocytes and the additionally delivered components can enhance healing. For example, MSCs are also believed to possess immunosuppression and anti-inflammatory effects. Chen et al., Athritis Res Ther. 2008; 10(5)223.

Alternatively, the synovial villi may be treated to further isolate or expand its beneficial cocktail of cells, components, tissue and the like. As introduced, this "cocktail" of the multiple tissue types and cells obtained from the synovial villi have healing potential in articular and meniscal cartilage as well as ligaments. The cocktail of beneficial cells can include cells such as synovial cells, red blood cells, angioblasts, white blood cells, fibroblasts, fat cells, stem cells, progenitor cells and the like. Similarly, if desired, cells may be separated from the synovial villi, followed by taking an aliquot to grow out so as to identify the cell types in the cocktail by culturing procedures and assays known in the art. Optionally, the separated cells can be analyzed by epitope labelling and flow cytometry. The cells can optionally be frozen and stored by protocols known in the art and described in U.S. Pat. Nos. 5,004,681; 5,192,553; 6,461,645; 6,569,427 and 6,605,275 to Boyse et al. incorporated herein by reference in their entirety. Optionally, prior to harvesting the synovial villi or after introducing the separated cells into the damaged tissue, it is encompassed by the present invention that the cells are mobilized by a physical means. Any physical means including, but not limited to lithotripsy, MRI, and CAT can be used.

In some embodiments the harvested synovial villi are further cleansed with one or more washing solutions. Still further, the harvested synovial villi and optionally cellular components, such as stem cells, may be separated from the collected sample. For instance, since the aspiration can collect synovial fluid as wells as synovial villi, it may be preferred to selectively remove low weight compounds that potentially adversely affect the joint. In a preferred approach, synovial villi and cells free floating in the synovial fluid are selectively obtained by centrifugation of a collected sample. A related technique is disclosed in US 2007/0059372 to Johnson, which is incorporated herein by reference, where broadly an aspirate from a joint is collected, centrifuged and separated into a supernatant and sediment. The sediment or supernatant can then be selectively exposed to stimulating factors prior to introduction to the joint of the patient.

Populations of stem cells and progenitor cells can be selected or enriched by utilizing surface markers such as c-kit, CD34 and H-2K. Surface markers such as Lin are typically lacking, or expressed at very low levels, in stem cells, so Lin can be a negative selection marker. Such cells may be CD34+ Thy1+ lin−. Cell-surface antigens which can be used to positively or negatively select for undifferentiated hematopoietic stem cells include, but are not limited to, CD34+, CD59+, Thy1+, CD38 (low/−), c-kit (−/low), lin−. Positive selection of marrow for CD34+ CD33− hematopoietic progenitors, and use of c-kit ligand can be used for ex-vivo expansion of early hematopoietic progenitors.

CD34 antigen has been widely used to estimate the number of stem cells in a cell population and to enrich for stem cell populations. The CD34 antigen is an approximately 110-115 kilodalton monomeric cell surface glycoprotein that is expressed selectively on human hematopoietic progenitor cells. The partial amino acid of a highly purified CD34 antigen has been analyzed, and it was found that it had no significant sequence similarity with any previously described structures. The antigen is not a leukosialin/sialophorin family despite structural similarities, and from a cDNA clone for CD34 from a KG-1 cell library enriched using the anti-CD34 monoclonal antibodies MY10 and BI-3C5 it has been determined to be a sialomucin. Hematopoietic cell lines KG-1, KMT-2, AML-1, RPMI 8402, and MOLT 13 express a 2.7 kilobase CD34 transcript. The cDNA sequence codes for a 40 kilodalton type I integral membrane protein with nine potential N-linked and many potential O-linked glycosylation sites which is a type I transmembrane protein. The 28 kilobase CD34 gene includes eight exons mapped from the coding sequences. The CD34 transcription start site is 258 base pairs upstream of the start site of translation. Anti-CD34 monoclonal antibodies My10 and 8G12, known in the art, bind to two different epitopes of the CD34 antigen expressed on stem cells. Lineage-specific antigens CD71, CD33, CD10, and CD5 are lacking on progenitor cells which are not lineage committed (CD34+ CD38−). The CD34 antigen can be used to estimate stem cell enrichment. It is estimated that a minimum of approximately $2.5 \times 10^6$ CD34$^+$ progenitors per kilogram patient weight are needed for effective hematopoietic reconstitution during bone marrow transplantation procedures.

Although stem cells are preferably present in the synovial villi at harvest, in some instances the treatment method is supplemented by addition or delivery of additional stem cells or progenitor cells. In some embodiments stem cells are obtained or harvested from the synovial fluid from the same or different joint. As discussed, the presence of synovial villi in the joint is believed to correlate with the increased presence of stem cells free floating in the synovial fluid and thus the presence of synovial villi also suggest the same joint may also house stem cells within the fluid. The presence of synovial tissue clumps in the fluid correlated with synovial fluid MSCs. McGonagle et al., Rheumatology 2008 47(8):1114-1116. A higher prevalence of mesenchymal progenitor cells (MSCs) has been found in the synovial fluid of OA patients and is believed to originate from disrupted joint structures. Jones et al., Athritis Rheum. 2004; 50(3):817-27. Disrupted joint structures are also associated with the presence of synovial villi. Accordingly, the presence of synovial villi may also assist in identifying which joints may be appropriate for harvesting the synovial fluid for collection of stem cells. Once collected, MSCs may be cultured to enhance their reparative properties. For example, while MSCs obtained from the synovial fluid also have potential for cartilage repair, repair may be further enhanced when exposing the stem cells to TGF-β. Crawford et al., European Cells and Materials, vol 16, suppl. 2, 2008 (page 41). Further, once combined, the cocktail of cells may be used to treat the defect while reducing inflammation. MSCs are known to possess potent immunosuppression and anti-inflammatory effects. Chen et al., Arthritis Res Ther. 2008; 10(5):223. Synovial fluid MSCs are also believed to mediate the repair response in cruciate ligaments. McGonagle et al., Rheumatology 2008 47(8):1114-1116.

It has also been postulated that circulating marrow progenitor cells find their way to the local areas of injury for healing influence. Thus, it is believed that stem cells have the capacity to home in on specific tissues and engraft within the tissue. Accordingly, their delivery may require less precision than explants of synovial villi. The process is not thoroughly understood, however various adhesion receptors and ligands which mediate the cell-matrix and cell-cell binding have been studied (Quesenberry and Becker, Proc. Natl. Acad. Sci. USA, vol. 95, pp. 15155-15157 (1998)). Some of the adhesion molecules studied include L, P and E selecting, integrins, VCAM-1, ICAM-1, VLA-4, VLA-5, VLA-6, PECAM, and CD44. The cells can therefore be infused via a large-bore central venous catheter, whereupon the stem cells will home in to the tissue in need of repair. Alternatively, the cells can be surgically implanted at a specific site at or near the damaged tissue. Allogenic transplants require careful donor and recipient matching for major histocompatibility (HLA) antigens. In the case of stem cell transplantation for bone marrow reconstitution graft-versus-host disease (GVHD) must be considered.

Beneficial cells, such as stem cells, may also be harvested from the omentum and provided with the synovial villi. The greater omentum (also the great omentum, omentum majus) is a large fold of peritoneum that hangs down from the stomach, and extends from the stomach to the posterior abdominal wall after associating with the transverse colon. The greater omentum is the largest peritoneal fold. It consists of a double sheet of peritoneum, folded on itself so that it consists of four layers. The two layers which descend from the greater curvature of the stomach and commencement of the duodenum pass in front of the small intestines, sometimes as low as the pelvis; they then turn, and ascend again as far as the transverse colon, where they separate and enclose that part of the intestine. These individual layers may be easily demonstrated in the young subject, but in the adult they are more or less inseparably blended. The left border of the greater omentum is continuous with the gastrolienal ligament; its right border extends as far as the commencement of the duodenum. The greater omentum is usually thin, presents a cribriform appearance, and always contains some adipose tissue, which in obese people accumulates in considerable quantity. Between its two anterior layers, a short distance from the greater curvature of the stomach, is the anastomosis between the right and left gastroepiploic vessels.

It is known that the omentum is covered with a layer of flat and oval cells. The omentum cells have pleuripotential healing capacity, ranging from primitive fibroblasts to fibrous tissue to cartilage cells. Within the omentum are adipose tissue, blood vessels and lymphatics. There are white blood cells and red blood cells in the vessels. The blood vessels have angioblasts cells for potential healing. The fat contains stem cells. It is known that omentum will migrate to areas of disease or injury in the abdomen. Accordingly, embodiments of the invention include the use of omental explants in total, morcellized, or after in vitro culture, to effect the healing of various organs or tissue types, including cartilage associated conditions.

The synovial villi may be cultured in the presence of IGF-1 or the explant may be co-administered with IGF-1. It has been known for years that IGF-1 is chondroreparative. IGF-1 is believed to play a key role in cartilage homeostasis, balancing proteoglycan synthesis and breakdown. Schmidt et al., Osteoarthritis Cartilage, 2006 May; 14(5):403-12. The action of IGF-1 on chondrocytes is mediated through the IGF-1 receptor. Taylor et al., FEBS Lett. 1988; 236:33-8. Composites of chondrocytes and polymerized fibrin were supplemented with IGF-1 during arthroscopic repair of full-thickness defects in horses and were shown to improve the repair capabilities of chondrocyte-fibrin grafts. Fortier et al., J Bone and Joint Surg 2002 March; 84-B(2)276-288. Although IGF-1 is naturally present in the synovium (see Keyszer et al., J. Rheumatol. 1995 February; 22(2)271-81), the total IGF-1 in normal human synovial fluid is an order of magnitude lower than that in the serum. Schneiderman et al., Arch Biochem Biophys 1995 December; 324(1):173-88. However, IGF-1 has been shown to be elevated in the synovial fluid of patients with osteoarthritis, in contrast to decreased levels of IGF-II and neutral levels of IGFBP-3. Matsumoto et al., Journal of Clinical Endocrinology and Metabolism 1996; 81:150-5. Increased IGF-1 production by human osteoarthritic chondrocytes is not dependent on growth hormone action. Dore et al., Arthritis and Rheutism, 1995; 38(3):413-419. Thus, effective stimulation of IGF-1 may require additional experimentation.

While IGF-1 is believed to increase cartilage production, exogenous administration of IGF-1 as well as human growth hormone (HGH) posses risks to patient health. Although IGF-1 is believed to enhance proliferation of cells and thus may also enhance proliferation of chondrocytes, it is believed to do so by inhibiting apoptosis, which includes apoptosis of cancer cells. Smith et al., British Medical Journal, 2000; 321:847-48.

Insulin is known to bind to the IGF-1 receptor and to illicit significant responses in cartilage. Kellner et al., J Drug Target, 2001; 9(6):439-8. Thus, insulin may also be a promising approach for use with synovial villi derived explants. Administration of a slow release formulation of insulin was provided to cartilaginous explants, which resulted in the stimulation of proteoglycan (PG) synthesis, inhibition of PG release and nitric oxide production and overcame detrimental effects of interleukin Cai et al., Osteoarthritis Cartilage, 2002 September; 10(9):692-706. At one time it was believed that only the islet cells of the pancreas would produce insulin; however, many other cells are known to produce insulin under certain conditions. Adult stem cells from the intestine have been coverted into insulin-producing beta cells in the pancreas of diabetic mice. Suzuki, PNAS 10.1073/pnas.0936260100. Stem cells extracted from the spleen can change into insulin-producing pancreatic islet cells. Fasutman et al, Science 2003 November; 302; 1123-1127. Bone marrow stem cells transplanted into the pancreas can morph into insulin-producing beta cells. Mehbood et al., Journal of Clin. Investig. 2003 March; 111(6). Adult hepatic progenitor cells can be induced into insulin-producing cells. Nagata et al., Biochem. Byophys. Res. Commun. 318:625-630. Thus, the production of insulin may be approached using a variety of cell types found throughout the body given the proper environment.

In another approach, the explant is administered together with an anthocyanin or anthocyanidin and optionally dextrose or cultured prior to administration. Glucose may be used as a substitute for dextrose. When combined with dextrose, anthocyanins and anthocyandins have been shown in U.S. provisional patent application 61/142,070 to significantly improve the production of cartilage. Dextrose is preferably provided at about 10-12%. Stimulation of new cartilage may occur, in part, by increasing gene expression and production of IGF-1 as well as providing substrate for glucosamine in the building of the cartilage matrix. Exemplary anthocyanins for use in the invention include cyanidin-3-glucosidase or delphinidin-3-glucosidase, cyanidin-3-galactosidase, and pelargonidin-3-galactosidase. Exemplary anthocyanidins include cyanidin, delphinidin, pelargonidin, malvidin and petunidin. The potential role of anthocyanins and anthocyanidins for the co-treatment of cartilage associated disorders is to provide chondroprotective and chondronutritive activities, which may be transferred directly to a joint or joint capsule suffering from a cartilage-associated condition or injury. These beneficial activities correlate with the ability of the anthocyanin and anthocyandin to modulate the synovium, thereby increasing both IGF-1 gene expression and IGF-1 production. Thus, administering an anthocyanin or anthocyanidin-derived composition may permit an increase in IGF-1 using the patient's own chemistry. Though nonlimiting, increasing the availability of IGF-1 within the affected joint capsule is believed to counter soluble IGF-1 binding proteins in the affected region, and thus increase its availability for binding to receptor in or at the cartilage cell. IGF-1 is thus permitted to interact with cartilage cells to produce mucoplysaccharides for chondronutritive activity and chondrorepair and/or chondrorestoration. Further, by simulating the body's innate production of IGF-1 the present invention enhances the body's natural protective mechanism while avoiding potential adverse effects associated with administration of exogenous IGF-1 or human growth hormone (HGH). Still further, the rapid breakdown of the anthocyanin or anthocyanidin itself permits improved regulation of IGF-1 gene expression and production while ensuring its removal and thus eliminating potential downstream effects on other potential regulatory pathways. As such, the compositions and methods provide both efficacy and safety. Benefits derived from anthocyanins/anthocyanidins may also be due in part to their antioxidant activities. For instance, the scavenging of free radicals within the synovial fluid may prevent attack on cartilage, thereby providing chondroprotection.

Delivery or implantation of the explants to the affected joint may be accomplished by positioning the explants on or proximate to the site of injury. It may also be desirable to impact or push the implant against the site of injury, surrounding crevices and the like. Delivery may be under direct vision to a specific location; however, delivery may also be placed intra articular by arthrocentesis, rather than by open or arthroscopic surgery.

The synovial villi or components thereof may be provided alone or with an implantable surgical device. Suitable implantable devices can be formed, for example, from polymers, biological materials, metals, metal alloys, combinations thereof, or the like. The implantable can be smooth or porous (or porous coated) and may exhibit biomechanical desired properties (e.g., elasticity, resistance to axial loading or shear forces) similar to articular cartilage. Preferably, the implantable device is porous or pitted to assist in retaining the explanted villi or portions thereof. In some embodiments, the device is biodegradable or bioabsorbable and, in addition, can be adapted to receive injections. In some embodiments of the invention, the implantable surgical device is, for example, replacement fibrocartilage, a replacement meniscus, a replacement ligament or the like.

The skilled artisan will appreciate that a variety of materials find use in the practice of the present invention, including, but not limited to, plastics, metals, ceramics, biological materials (e.g., collagen or other extracellular matrix materials), hydroxyapatite, cells (e.g., stem cells, chondrocyte cells or the like), or combinations thereof. Based on the information (e.g., measurements) obtained regarding the tissue defect and the articular surface and/or the subchondral bone, a repair material can be formed or selected. The repair material may include any combination of materials, including at least one non-pliable material.

Currently, joint repair systems often employ metal and/or polymeric materials including, for example, prosthesis which are anchored into the underlying bone (e.g., a femur in the case of a knee prosthesis). See, e.g., U.S. Pat. Nos. 6,203,576 and 6,322,588. A wide-variety of metals and metal alloys may find use in the practice of the present invention, and may be selected based on any criteria, for example, based on resiliency to impart a desired degree of rigidity. Further, suitable synthetic polymers can include, for example, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Bioabsorbable or biodegradable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly(dimethyl glycolic acid), poly(hydroxy butyrate), and similar copolymers may also be used. Polymers can be prepared by any of a variety of approaches including conventional polymer processing methods. Preferred approaches include, for example, injection molding, which is suitable for the production of polymer components with significant structural features, and rapid prototyping approaches, such as reaction injection molding and stereo-lithography. The substrate can be textured or made porous by either physical abrasion or chemical alteration to facilitate incorporation of the metal coating.

Naturally the skilled artisan will appreciate that more than one metal and/or polymer can be used in combination with each other. For example, one or more metal-containing substrates may be coated with polymers in one or more regions or, alternatively, one or more polymer-containing substrate may be coated in one or more regions with one or more metals.

In embodiments comprising a coating, the coating can be applied by surrounding a core with powdered polymer and heating until cured to form a coating with an internal network of interconnected pores. The tortuosity of the pores (e.g., a measure of length to diameter of the paths through the pores) can be important in evaluating the probable success of such a coating in use on a prosthetic device. See, also, Morris U.S. Pat. No. 4,213,816. The porous coating can be applied in the form of a powder and the article as a whole subjected to an elevated temperature that bonds the powder to the substrate. Selection of suitable polymers and/or powder coatings can be determined in view of the teachings and references cited herein, for example based on the melt index of each.

One or more regions of an implantable surgical device (e.g., the outer margin of the superficial portion and/or the deep portion) can be biodegradable or bioabsorbable, for example to allow the interface between the articular surface repair system and the patient's normal cartilage, over time, to be filled in with hyaline or fibrocartilage. Similarly, one or more regions (e.g., the outer margin of the superficial portion of the articular surface repair system and/or the deep portion) can be porous. The degree of porosity can change throughout the porous region, linearly or non-linearly, for where the degree of porosity will typically decrease towards the center of the articular surface repair system. The pores can be designed for in-growth of cartilage cells, cartilage matrix, and connective tissue thereby achieving a smooth interface between the articular surface repair system and the surrounding cartilage.

In certain embodiments, devices of the invention are attached to the patient's bone. In such instances attachment may be performed using of a cement-like material such as methylmethacrylate, injectable hydroxy- or calcium-apatite materials and the like.

C. Devices for the Selective Harvesting of Synovial Villi and Delivering of Explants Though harvesting synovial villi and delivery of explants can be accomplished using a variety of methods and tools, the invention also includes devices and apparatuses particularly useful for harvest, collection and delivery of synovial villi. Among the beneficial objects of the invention is the selective harvesting of protrusions of the synovium identifiable within a patient's joint. That is, the anatomical nature of synovial villi lends to their capture. As such, tools are presented which are developed to effectively harvest synovial villi from the synovial lining and to deliver the explants to the desired location. Harvest, collection and delivery tools may be hand operated, mechanized or motorized as desired by the user. As an example, a synovial resector attached to standard motorized instrumentation could effectively harvest synovim; however, as a base design it may also damage surround fibrous tissue. Further, a delivery instrument could be as simple as a syringe and needle; however, traditional needles do not effectively reposition an explant or permit the synovial villi to be pushed into pits or crevices. Moreover, the collected material could be delivered in an autogenous fibrin blood clot, via a biodegradable or bioabsorbable sponge, or injected under a patch of autogenous tissue.

Figure 1:
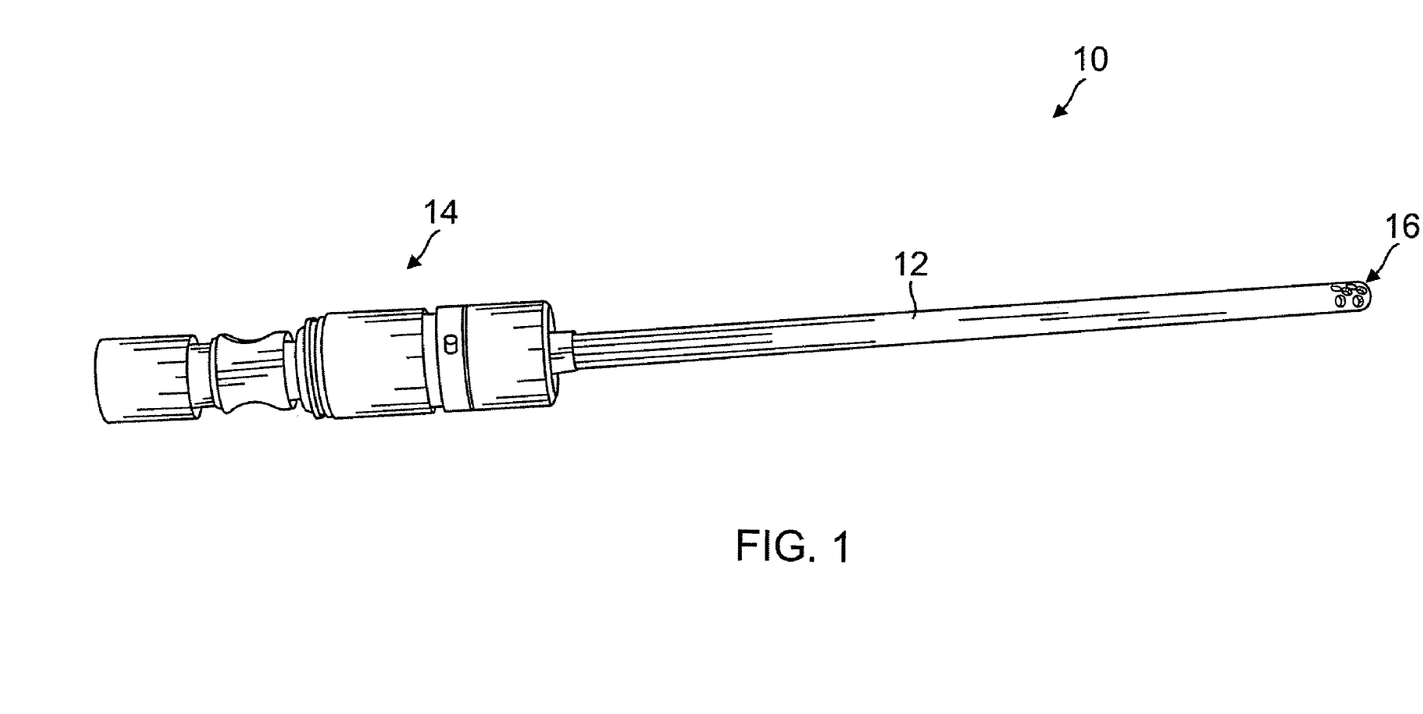
FIG. 1 is a perspective view of a basic harvesting device 10 that may be used to harvest synovial villi via a plurality of apertures 16.
Figure 2:
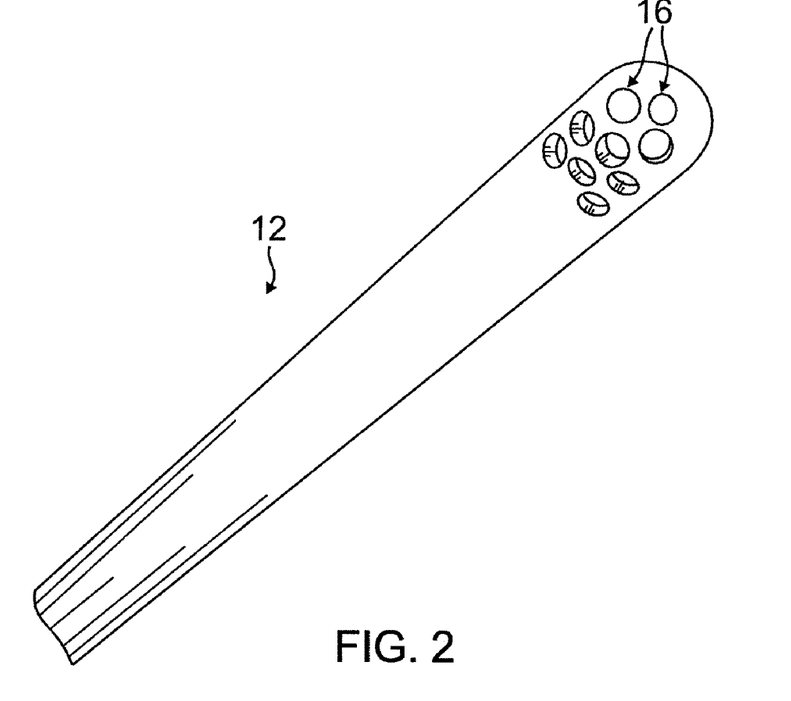
FIG. 2 is the distal end of the shaft 12 depicted in FIG. 1 showing a plurality of apertures 16 for receiving synovial villi.
Figure 3:
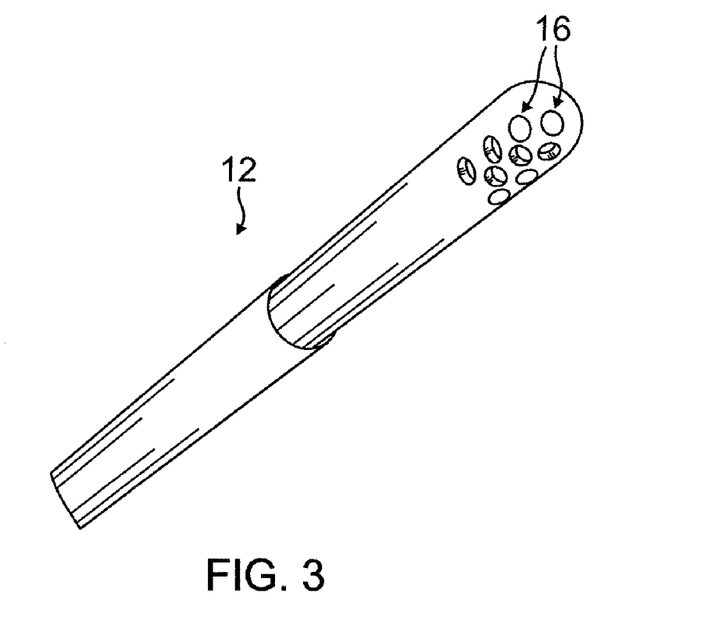
FIG. 3 is an alternative distal end of the shaft 12 having a smaller size than that shown in FIG. 2.

In a preferred embodiment tools are adapted for use with motorized instrumentation used in arthroscopy. A basic harvesting tool 10 is depicted in FIG. 1, which includes an elongated shaft 12 having at its proximal end a handle portion 14, which may be attached to a vacuum source and at its distal end a plurality of apertures 16 able to receive synovial villi. FIGS. 2 and 3 are enlarged views of the shaft 12 and its plurality of apertures 16 for collection of synovial where FIG. 3 provides a smaller version than depicted in FIG. 2 and thus demonstrates the device may be provided in a range of sizes as desired by the user. Though depicted as generally circular, the apertures 16 may be provided in any suitable geometry and size, which permits the insertion of synovial villi. Thus, the apertures 16 may be rounded, triangular, square, pentagonal and the like or may be provided as a series of one or more slits. Sizing of the apertures 16 are such that synovial villi may be received; however, preferably the apertures 16 are not overly large to damage the surrounding base membrane. That is, while surgical devices with larger openings exist, they would tend to pull along the synovium surrounding the targeted region of villi to varying degrees making repair and healing longer. Further, enlarged apertures 16 would tend to pull and damage mature fibrous tissue that may be of no therapeutic value yet compromise the joint capsule integrity. For instance, devices having collecting apertures 16 greater than about 4 or 5 mm tend to risk violating the joint capsule. In extreme situations, enlarged apertures 16 may lead to synovial hernia or leak of synovial fluid post op. Accordingly, preferred apertures 16 have a diameter less than 4 mm, more preferably between about 1 mm and 2 mm.

Figure 4:
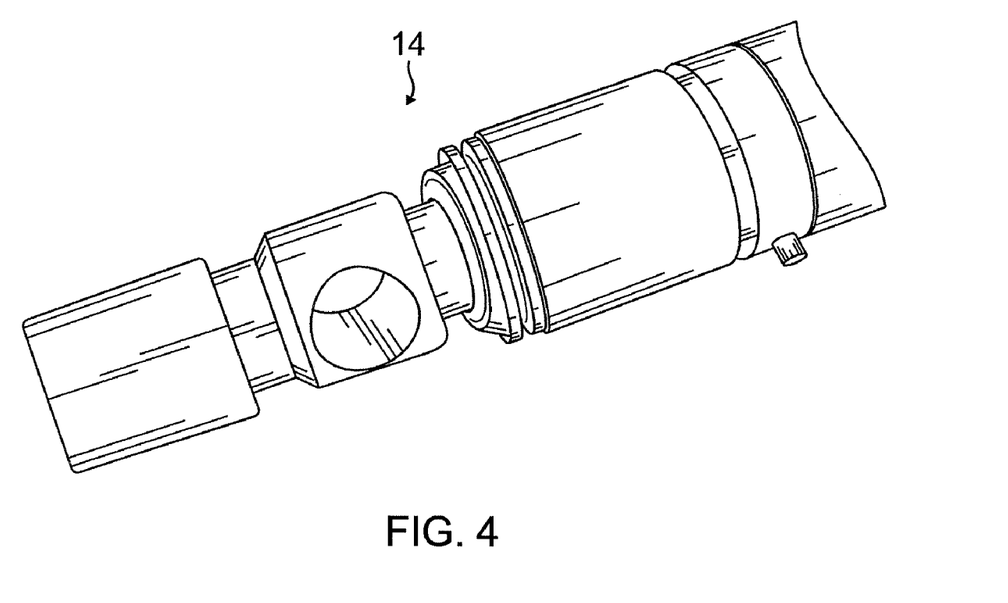
FIG. 4 is a perspective view of the proximal end or handle 14 of the harvesting device 10 depicted in FIG. 1.
Figure 5:
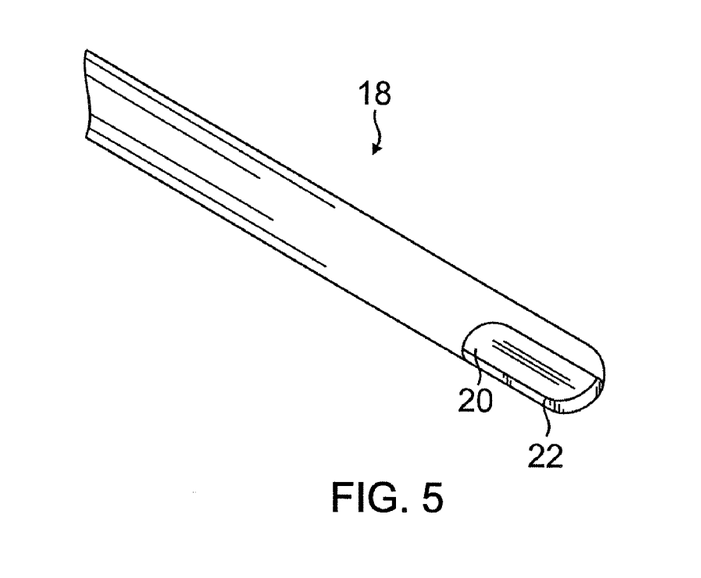
FIG. 5 is a cutting means with collecting aperture 20 and sharp edge 22 for insertion into the shaft 12 as depicted in FIG. 2.

FIG. 4 provides an enlarged view of an exemplary handle 14, which may be attached to a vacuum or suction source to assist in insertion of synovial villi into the apertures 16 and may be adapted for activating a cutting means to excise synovial villi at the site of harvest. Thus, the handle 14 may also any number of switches, triggers, dials, guages and the like to selectively activate or adjust a number of features such as suction, manipulation of the cutting means, washing and the like. FIG. 5 depicts a hollow shaft 18 having an exemplary cutting means, which is depicted as a collecting aperture 20 and sharp edge 22. Referring to FIGS. 1-8d collectively, in a preferred embodiment, the hollow shaft 18 with cutting means is housed within the elongated shaft 12 of the harvesting tool 10. A medium, such as a fluid or air, is drawn into the plurality of apertures 16 thereby drawing in the protruding villi. Once drawn into the apertures 16, the cutting means may be rotated or actuate via a pistoning method to excise the villi from the synovium. Rotation or pistoning action can be actuated manually; however, motorizing the action is preferred. The excised synovial villi can then be collected through suction into a capturing trap or may be removed directly from the cutting means.

Figure 6:
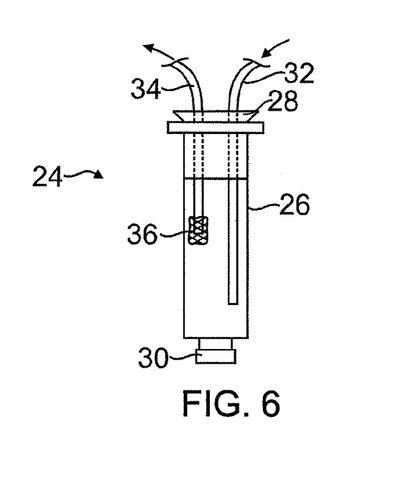
FIG. 6 is a front plan view depicting a device provided in collection configuration 24 for collecting synovial villi.

The harvesting device 10 may be coupled to a second apparatus for collection and/or delivery of the explants. Accordingly, in a related embodiment of the invention harvesting and delivery of synovial villi is performed using an apparatus having a collection configuration 24 and a delivery configuration 40. Optionally, this apparatus is coupled to a harvesting tool 10. An exemplary collection and delivery apparatus is depicted in FIGS. 6-8d. For instance, FIG. 6 depicts a collection configuration 24, where a syringe body 26 includes a removable stopper 28 having at least two apertures to form an aspiration trap and a capped luer connector 30 at the opposing end. Though a luer connector 30 is depicted, any suitable connecting structure is suitable. Synovial villi and optionally synovial fluid is aspirated into the syringe body 26 through a hollow collection shaft 32, which itself may be coupled to the harvesting tool 10 to facilitate collection. Further, a vacuum tube 34 is coupled to the second of the at least two apertures and operably attached to a vacuum source to generate desired suction. Although not required, in a preferred embodiment the hollow collection shaft 32 extends downward into the syringe body 26 farther than the vacuum tube 34. This configuration may assist in delivering the collected sample into the syringe body 26, yet prevent entry of the sample into the vacuum tube 34. In some embodiments, the synovial villi are permitted to settle towards the bottom of the syringe body 26, while an aspirating media is permitted to exit the syringe body 26 via the vacuum. In a preferred embodiment a screen 36 is positioned around the vacuum tube 34 to prevent or reduce the harvested material from entering the vacuum tube 34.

Figure 7:
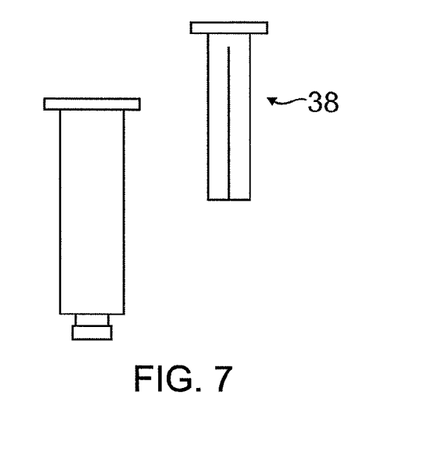
FIG. 7 is a front plan view depicting the interchangeability between useable configurations, which demonstrates a removable syringe plunger 38.

Once collected in the syringe body 26, the harvested synovial villi can be removed for further culturing by removing the stopper 28 and transferred the sample into a culturing dish. FIG. 7 depicts the stopper 28 removed as well as a removable plunger 38 removed. This permits the collected synovial villi to be pretreated with therapeutics prior to re implantation. For example, the synovial villi may be treated with IGF-1, TGF-β, an anthocyanin or anthocyanidin, dextrose, a stimulatory factor and the like. Alternatively, the sample may be centrifuged for collection of a sediment or supernatant. The sediment may be washed or cleansed. After which the sample may be added to a syringe body 26 for delivery to the patient. Therapeutics may be co-added for co-delivery.

Figure 8A:
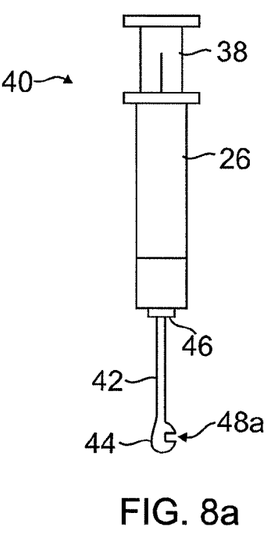
Figure 8B:
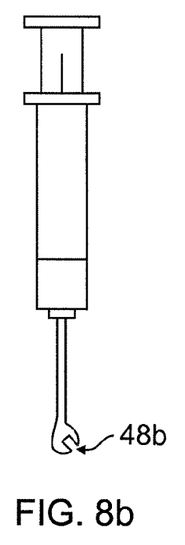
FIG. 8b depicts a delivery aperture at 135 degrees 48b.
Figure 8C:
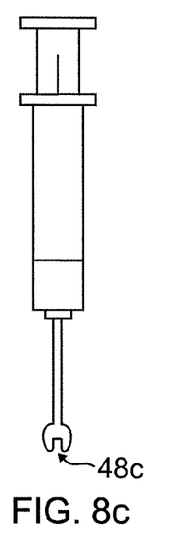
FIG. 8c depicts a delivery aperture at 180 degrees 48c.
Figure 8D:
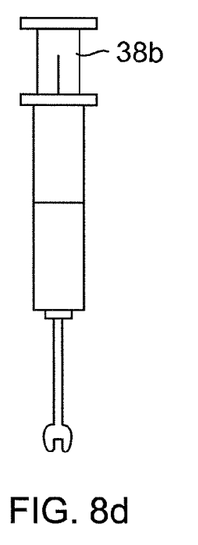
FIG. 8d depicts a shortened plunger 38b.

Exemplary delivery configurations 40 are provided in FIGS. 8a-d. Referring collectively to FIGS. 8a-d, a delivery needle 42 having a bulbous end 44 is attached to the syringe body 26, such as via a luer connector 46. A syringe plunger 38 is inserted into the syringe body 26 and downward pressure delivers the explant collected within the syringe body 26 outward through the bulbous end 44. The bulbous end 44 may be provided in a variety of configurations such as to deliver sample at 90 degrees 48a (see FIG. 8a), 135 degrees 48b (see FIG. 8b), 180 degrees 48c (see FIG. 8c) or any desired angle. A bulbous end 44 having a delivery aperture of about 90 degrees 48a to about 135 degrees 48b is preferred. Such configurations tend to improve delivery by placing the needle proximate to the treatment area while permitting the user to move, spread or press the delivered sample to the desired region without substantially piercing the surrounding tissue. As such, the bulbous end 44 permits the user to physically force or impact the explants and/or therapeutics at a desired region or depression in the organ or tissue surface. Delivery is preferably under direct vision to a specific or predetermined location; however, delivery may be performed intra-articularly by arthrocentesis, rather than by open or athroscopic surgery. The skilled artisan will understand the depressions may be anatomical, pathological or surgically created. In some embodiments the synovial villi are placed in a meniscal tear prior to suturing to provide the cellular and necessary nutrients to enhance repair. The skilled artisan will also recognize the needle gauge may vary depending on the needs or preferences of the user. The needle 42 may be constructed from any suitable material such as metal, metal alloy, polymer plastic and the like and may be transparent or opaque. Further, while a generally round or oval bulbous end 44 is presently preferred any suitable geometry may be adapted for use, such as square, triangular, a polygon and the like. That is, preferably the bulbous end 44 is not sharpened to a point to reduce piercing of the tissue. Further, the skilled artisan will likely consider the preferred needle 42 to be disposable; however, reusable needles 42 are also suitable. Depending on the sample or condition of the patient, the user may wish to deliver the entire volume within the syringe body 26 or less than the entire volume. When delivering less than the entire volume contained in the syringe body the plunger may be shortened 38b as depicted in FIG. 8d. Alternatively the plunger 38 may be only partially depressed.

The delivery configuration 40 depicted in FIGS. 8a-d could also act as a harvesting tool. In such an embodiment the syringe body 26 with needle 42 is position next to the targeted synovial villi while the suction draws the villi through the needle 42 and into the syringe body 26. Further, the bulbous end 44 can be used to protect the underlying synovial base layer by providing a blunt end compared to a traditional needle.

Harvest, collection or delivery devices may be combined or provided as a surgical kit for performing surgical procedures. In preferred embodiments the surgical kit includes a harvesting tool for selective harvest of synovial villi from a synovial lining of a joint, the harvesting tool including a shaft having at one end a plurality of apertures for receiving synovial villi and a cutting means for surgical removal of received villi; a needle including a proximal end adapted for attachment to a syringe body and a bulbous distal end having a delivery aperture. The surgical kit may also include a syringe, such as a disposable syringe, a syringe stopper, transfer tubing and connectors and the like to communicatively join harvesting and delivery devices as well as to join the devices to a vacuum or the like. The surgical kit can be used in arthroscopic surgery. The kit may also include implantable or surgical devices, such as a bioabsorbable sponge, a replacement meniscus, a variety of matrix materials for filling or dressing and the like.

D. Replacement Meniscus

White fibrocartilage consists of a mixture of white fibrous tissue and cartilaginous tissue in various proportions. It is the only type of cartilage that contains type I collagen in addition to the normal type II. White fibrocartilage is composed of fibrous connective tissue arranged in bundles, with chondrocytes between the bundles; the cells to a certain extent resemble tendon cells or dense regular connective tissue. Fibrocartilage is found in the pubic symphysis, intervertebral discs, and the meniscus, such as, for example, the knee, acromioclavicular, sternoclavicular, and temporomandibular joints.

As an overview, an exemplary method includes harvesting synovial villi from a joint of the patient, optionally culturing or isolating components from the synovial villi, to form an explant and delivering the explant to the fibrocartilage defect. Delivery may include use of the above described apparatus having a syringe body and bulbous end for dispersing the sample and spreading the sample as desired or pressing the sample against the area of the defect.

The methods and devices are particularly useful when used together with a replacement meniscus. The replacement meniscus can be used to replace the, for example, sternoclavicular meniscus, acromioclavicular meniscus, temporomandibular meniscus, radioulnar meniscus, and the like.

In the knee, the meniscus is a C-shaped piece of fibrocartilage located at the peripheral aspect of the knee joint, providing lubrication and nutrition to the joint. Each knee has two menisci, medial and lateral, whose purpose is to provide space between the tibia and the femur, thus preventing friction and allowing for the diffusion of articular cartilage. The majority of the meniscus has no blood supply, and thus if it is damaged, from trauma or age, it is unable to undergo the body's normal healing process. Damaged portions can move inside the joint, get caught between the bones, and cause pain, swelling, and decreased mobility. Current treatments for a damaged meniscus include repair, removal, and transplantation.

During conventional repair, the tissues are held together long enough for biological healing to occur. An exemplary procedure involves threading long needles into the meniscus and out an incision in the back of the knee. The suture thread ends are tied together on the outside of the knee capsule layer to bring the tear together. In such instances, synovial villi may be placed at the meniscal tear prior to suturing to provide cellular or necessary nutrients to enhance repair. However, the majority of meniscal tears are not suitable for repair and instead the torn piece is removed, known as a meniscectomy. The torn portion of the meniscus is excised, leaving behind as much normal meniscal cartilage as possible. The remaining meniscal rim is then rebalanced and contoured to provide a more natural shape. Thus, synovial villi may be delivered to the remaining meniscus to enhance healing.

In certain cases, the meniscal tear is so extensive that the entire meniscus must be removed, leaving the joint prone to constant pain and swelling. Further, removal of the meniscus cartilage leads to progressive, degenerative arthritis of the knee joint. Replacing the badly damaged or deficient meniscus restores normal knee structure and helps protect the remaining joint surfaces.

Accordingly, the invention includes a replacement meniscus that includes an explant including or derived from harvested synovial villi. The replacement meniscus can be made of any suitable material, such as, for example, collagen. In embodiments made of collagen, the collagen can be, for example, type 1 collagen, or the like. In other embodiments the replacement meniscus can be made of, for example, a porous polymer, bacterial cellulose gel, a bioplastic, porcine small intestinal submucosa, polyvinyl alcohol-hydrogel (PVA-H), or the like.

In a related embodiment the invention includes a method of making a replacement meniscus, including harvesting of synovial villi and optionally isolating, expanding or culturing the synovial villi to obtain a desired cell or biological component population; and combining the sample together with a biologically compatible replacement meniscus.

E. Replacement Ligament

Though often discussed in terms of repair of cartilage, the invention is also effective in the treatment of ligaments. For example, the synovial villi are effective at enhancing repair of cruciate ligaments or collateral ligaments of the knee. Further, synovial villi are effective at enhancing repair of the hip labrum or ligamentous tears of the hip. Further, synovial villi are effective at augmenting repair of a torn capsular ligament of the shoulder or rotator cuff of the shoulder.

Conventionally, damaged anterior cruciate ligaments are replaced with grafts from other patient tissue, such as tendon tissue. However, in certain circumstances, the fixation of the replacement ligament is not adequate, requiring further surgery. Prosthetic devices have been used in place of natural connecting tissue, but these devices also exhibit unsatisfactory fixation. Further, the prosthetic devices do not function as would the natural anterior cruciate ligament. Accordingly, various approaches have been developed to improve replacement ligaments, which reproduce the function of a natural collateral or cruciate ligament.

Central to such approaches is to provide materials or substrates that facilitate growth of new cells. For instance, braided materials or those having different porosities can provide suitable substrates to encourage cell and thus tissue growth. Accordingly, combining such substrates with synovial villi-derived explants further accelerates healing. Thus, in the invention the replacement ligament may be combined or cultured in the presence of harvested synovial villi to encourage attachment or ingrowth of beneficial cells.

The biological replacement ligament may then be attached to bone in a way consistent with its design. For instance, a bore may be provided in a bone at the region where the original ligament was attached. Then one end of the replacement ligament is inserted into the bore. Next, a bone plug or another plug of permanent or bioabsorbable material is inserted into the opposing end of the replacement ligament. The skilled artisan will consider other fixation devices may also be employed such as the use of fasteners or the use of a wedge member.

EXAMPLES

Example 1

Harvesting Synovial Villi from the Knee

As a pilot study synovial villi are removed from synovium from total knee patient. The synovium is surgically removed and placed in a Ringer's lactate bath. Synovial villi are removed from the synovium using arthroscopic equipment. The collected material is placed in the meniscal and articular cartilage explants for later use.

Example 2

Storage of Cells Obtained from Harvested Synovial Villi

Samples harvested or collected from synovial villi may be frozen for later use or analysis. Fresh freezing medium is prepared by mixing 80% FCS and 20% DMSO. Cryovials are pre-chilled to −70 C in a Nalgene freezing box and cultured cells at a concentration of between $5\times10^5$ and $1\times10^6$ cells/mL are harvested with trypsin-EDTA. The cell/media material is centrifuged for 5' at 3500 rpm. The majority of the media is removed by aspiration and the cells are chilled on ice for 1-2'. The final cell pellet is re-suspended in ice-cold freezing medium. The cell solution (0.5 mL per cryovial) is transferred into the pre-chilled cryovials in the freezing box. The freezing box containing the cryovials is placed in a −70 C freezer. Twenty four (24) hours after the cryovials are placed in the freezer, the frozen cells are transferred to liquid nitrogen for long term storage.

Example 3

Meniscus Replacement

After determining that the patient is a suitable candidate for meniscus replacement, the replacement meniscus is prepared. Synovial villi are identified in a joint of the patient and are harvested. They synovial villi are morcellized and placed into a biologically compatible replacement meniscus. The replacement meniscus is made from type 1 collagen. The replacement (containing the cells) is then placed into an appropriate tissue culture medium and maintained under aseptic conditions.

The patient is prepared for surgery using typical procedures. After the anesthetic is administered and knee examined, a tourniquet is placed on the upper thigh and the thigh is secured to the table in a padded limb holder. The knee and lower leg are cleansed and draped and a diagnostic arthroscopy is performed. The instruments are inserted through three to four 1 cm incisions around the knee. One incision is for sterile saline inflow, used to improve visualization within the joint. An inspection of the gliding surfaces in the region of the previously removed meniscus is important to make sure arthritic changes have not yet become advanced enough to preclude the meniscus replacement. The remainder of the meniscus is removed with arthroscopic instruments. A two to three inch vertical incision is made, and a trough cut into the tibia (shin bone) where the native meniscus attached. The replacement meniscus, of the appropriate size as determined from radiographic measurements, is prepared with a similarly sized bone bridge connecting the front and back meniscus attachments to bone. The new meniscus is press fit into the bone trough and secured into the trough as necessary with sutures or absorbable pins. The periphery of the meniscus is then repaired to the adjacent joint capsule with sutures similar to a meniscus repair.

Postoperative rehabilitation goals include full straightening of the knee, decreasing the swelling, and regaining control of the quadriceps muscle. Patients are encouraged to perform straight leg raises in the brace shortly after surgery. The brace, with the knee in extension, is used to walk for six weeks. Range of motion rehabilitation, from 0-90 degrees, is generally started soon after surgery, without any weight-bearing during motion. The brace is unlocked six weeks post-surgery and removed entirely after eight weeks, typically when good quadriceps control is demonstrated.

Motion is increased as tolerated at six weeks, but deep squats are avoided until 12 weeks. Low impact activities such as swimming and exercise machines are encouraged at 12 weeks, with advancement to cutting and pivoting sports generally at 16 weeks.

Example 4

Ligament Replacement

After determining that the patient is a suitable candidate for ligament replacement, the replacement ligament is prepared. An explant of synovial villi is harvested from the patient, minced and placed into a biologically compatible replacement ligament. For this example, the ligament includes a compressible core of resilient material formed as a unitary mass; and a separate, flexible outer sheath. The replacement ligament containing the explant is then placed into an appropriate tissue culture medium and maintained under aseptic conditions.

The patient is prepared for surgery using typical procedures. After the anesthetic is administered and knee examined, a tourniquet is placed on the upper thigh and the thigh is secured to the table in a padded limb holder. The knee and lower leg are cleansed and draped and a diagnostic arthroscopy is performed. The instruments are inserted through appropriate incisions around the knee. One incision is for sterile saline inflow, used to improve visualization within the joint. The replacement ligament together with the synovial villi is sutured to remaining portions of the natural ligament.

Postoperative rehabilitation goals include full straightening of the knee, decreasing the swelling, and regaining control of the quadriceps muscle. Patients are encouraged to perform straight leg raises in the brace shortly after surgery. The brace, with the knee in extension, is used to walk for six weeks. Range of motion rehabilitation, from 0-90 degrees, is generally started soon after surgery, without any weight-bearing during motion. The brace is unlocked six weeks post-surgery and removed entirely after eight weeks, typically when good quadriceps control is demonstrated.

What is claimed is:

1. A method for treating a patient to repair damaged or diseased tissue, comprising:
   a) harvesting synovial villi from a synovial membrane of a joint of the patient to provide an explant;
   b) introducing the explant to an implantable surgical device; and
   c) implanting the surgical device so as to repair the damaged or diseased tissue, wherein the implanted surgical device comprises synovial villi and all of its harvested components.

2. The method according to claim 1, wherein the implantable surgical device comprises a replacement meniscus.

3. The method according to claim 2, wherein the meniscus comprises a biocompatible material.

4. The method according to claim 2, wherein the meniscus comprises collagen or a type 1 collagen.

5. The method according to claim 2, wherein the meniscus comprises a porous polymer.

6. The method according to claim 2, wherein the meniscus comprises a bioplastic.

7. The method according to claim 1, wherein the damaged tissue is selected from the group consisting of a sternoclavicular meniscus, an acromioclavicular meniscus, a tempromandibular meniscus, and a radioulnar meniscus.

8. The method according to claim 1, wherein the damaged tissue is a joint labrum, a shoulder labrum or hip labrum.

9. The method according to claim 1, further comprising performing microfracture surgery on the patient.

10. The method according to claim 1, further comprising performing arthroscopic abrasion surgery on the patient.

11. The method according to claim 1, further comprising performing arthroplasty surgery on the patient.

12. The method according to claim 1, wherein the implantable surgical device comprises a replacement ligament.

13. The method according to claim 1, further comprising culturing the explant in the presence of IGF-1.

14. The method of claim 1, further comprising a step of morcellizing the explant prior to the step of introducing the explant to the implantable surgical device.

15. The method of claim 1, further comprising a step of culturing the explant ex vivo prior to the step of introducing the explant to the implantable surgical device.

16. The method according to claim 1, wherein the step of harvesting synovial villi comprises excising at least 50% of the entire villous protrusion extending into the joint cavity.

17. The method according to claim 1, wherein the step of harvesting synovial villi comprises selectively harvesting villous protrusions to prevent or reduce harvest of a base synovial membrane disposed between the synovial villi in the joint.

18. The method according to claim 1, wherein the step of harvesting synovial villi is performed using a harvesting tool comprising a hollow shaft having at one end a plurality of apertures for receiving synovial villi and a cutting means for surgical removal of received villi from a base synovial membrane.

19. The method according to claim 1, wherein the step of harvesting synovial villi comprises a joint aspiration step, wherein portions of synovial villi are collected from an aspirate.

20. The method according to claim 19, wherein the portions of synovial villi are collected in a trap comprising a syringe body.

21. The method according to claim 1, wherein the introduced explant comprises synovial cells, fibroblasts, lymphocytes and angioblasts.

22. The method according to claim 1, wherein the introduced explant comprises blood vessels comprising whole blood.

23. The method according to claim 22, wherein the introduced explant comprises red blood cells, white blood cells, angioblasts, electrolytes, clotting factors, fibrinogen, growth hormones and growth factors.

24. The method according to claim 23, wherein the growth factors comprise IGF-1.

25. The method according to claim 1, wherein the introduced explant comprises adipose tissue.

26. The method according to claim 1, further comprising treating the explant with a mixture comprising an anthocyanin or an anthocyanidin.

27. The method according to claim 1, further comprising a step of introducing an anthocyanin or anthocyanidin to the damaged tissue.

* * * * *